United States Patent
David

(10) Patent No.: US 10,426,788 B2
(45) Date of Patent: Oct. 1, 2019

(54) CHEMICAL ENTITIES THAT KILL SENESCENT CELLS FOR USE IN TREATING AGE-RELATED DISEASE

(71) Applicant: Unity Biotechnology, Inc., Brisbane, CA (US)

(72) Inventor: Nathaniel David, Brisbane, CA (US)

(73) Assignee: Unity Biotechnology, Inc., Brisbane, CA (US)

(*) Notice: Subject to any disclaimer, the term of this patent is extended or adjusted under 35 U.S.C. 154(b) by 10 days.

(21) Appl. No.: 15/915,989

(22) Filed: Mar. 8, 2018

(65) Prior Publication Data

US 2018/0193359 A1 Jul. 12, 2018

Related U.S. Application Data

(63) Continuation of application No. 15/069,769, filed on Mar. 14, 2016, now Pat. No. 10,195,213.

(60) Provisional application No. 62/177,434, filed on Mar. 13, 2015.

(51) Int. Cl.
| | |
|---|---|
| *A61K 31/352* | (2006.01) |
| *A61K 31/575* | (2006.01) |
| *A61K 9/00* | (2006.01) |
| *A61K 31/4025* | (2006.01) |
| *A61K 31/365* | (2006.01) |
| *A61K 31/167* | (2006.01) |
| *A61K 31/541* | (2006.01) |
| *A61K 31/4709* | (2006.01) |
| *A61K 31/4741* | (2006.01) |
| *A61K 31/426* | (2006.01) |
| *A61K 31/427* | (2006.01) |
| *A61K 31/433* | (2006.01) |
| *A61K 31/496* | (2006.01) |
| *A61K 31/05* | (2006.01) |
| *A61K 31/138* | (2006.01) |
| *A61K 31/4178* | (2006.01) |
| *A61K 31/11* | (2006.01) |
| *A61K 31/122* | (2006.01) |
| *A61K 31/166* | (2006.01) |

(52) U.S. Cl.
CPC .......... *A61K 31/575* (2013.01); *A61K 9/0019* (2013.01); *A61K 31/05* (2013.01); *A61K 31/11* (2013.01); *A61K 31/122* (2013.01); *A61K 31/138* (2013.01); *A61K 31/166* (2013.01); *A61K 31/167* (2013.01); *A61K 31/352* (2013.01); *A61K 31/365* (2013.01); *A61K 31/4025* (2013.01); *A61K 31/4178* (2013.01); *A61K 31/426* (2013.01); *A61K 31/427* (2013.01); *A61K 31/433* (2013.01); *A61K 31/4709* (2013.01); *A61K 31/4741* (2013.01); *A61K 31/496* (2013.01); *A61K 31/541* (2013.01)

(58) Field of Classification Search
None
See application file for complete search history.

(56) References Cited

U.S. PATENT DOCUMENTS

| | | |
|---|---|---|
| 6,277,844 B1 | 8/2001 | Spector et al. |
| 6,492,389 B1 | 12/2002 | Huang et al. |
| 6,703,382 B2 | 3/2004 | Wang et al. |
| 7,390,799 B2 | 6/2008 | Bruncko et al. |
| 7,642,260 B2 | 1/2010 | Bruncko et al. |
| 7,709,467 B2 | 5/2010 | Bruncko et al. |
| 7,714,005 B2 | 5/2010 | Chen et al. |
| 7,767,684 B2 | 8/2010 | Bruncko et al. |
| 7,842,681 B2 | 11/2010 | Elmore et al. |
| 7,857,804 B2 | 12/2010 | McCaffrey et al. |
| 7,906,505 B2 | 3/2011 | Bruncko et al. |
| 7,973,161 B2 | 7/2011 | Bruncko et al. |
| 8,034,779 B2 | 10/2011 | Distelhorst et al. |
| 8,039,668 B2 | 10/2011 | Pellecchia |
| 8,114,893 B2 | 2/2012 | Baell et al. |
| 8,168,645 B2 | 5/2012 | Baell et al. |
| 8,188,077 B2 | 5/2012 | Ding et al. |
| 8,232,273 B2 | 7/2012 | Baell et al. |
| 8,338,466 B2 | 12/2012 | Kunzer et al. |
| 8,343,967 B2 | 1/2013 | Ding et al. |
| 8,426,422 B2 | 4/2013 | Hexamer et al. |
| 8,501,992 B2 | 8/2013 | Kim et al. |
| 8,518,970 B2 | 8/2013 | Baell et al. |
| 8,546,399 B2 | 10/2013 | Bruncko et al. |
| 8,557,983 B2 | 10/2013 | Bruncko et al. |
| 8,563,735 B2 | 10/2013 | Bruncko et al. |
| 8,580,794 B2 | 11/2013 | Bruncko et al. |
| 8,586,754 B2 | 11/2013 | Bruncko et al. |
| 8,614,318 B2 | 12/2013 | Bruncko et al. |

(Continued)

FOREIGN PATENT DOCUMENTS

| | | |
|---|---|---|
| WO | WO-03028443 A1 | 4/2003 |
| WO | WO-2005112951 A1 | 12/2005 |

(Continued)

OTHER PUBLICATIONS

Billard. BH3 mimetics: status of the field and new developments. Mol Cancer Ther. Sep. 2013;12(9):1691-700. Epub Aug. 23, 2013.

(Continued)

*Primary Examiner* — Samantha L Shterengarts

(74) *Attorney, Agent, or Firm* — Rudy J. Ng; Michael Schiff; Janet Martineau

(57) ABSTRACT

Disclosed herein are compounds that are effective for treatment of various disease states associated with senescence. The disclosed compounds can be used to eliminate senescent cells for disease treatment. The dosing of the compounds includes both single administration and regimens of cycling dosages.

8 Claims, No Drawings

(56) References Cited

U.S. PATENT DOCUMENTS

| | | |
|---|---|---|
| 8,624,027 B2 | 1/2014 | Shah et al. |
| 8,759,520 B2 | 6/2014 | East et al. |
| 8,809,352 B2 | 8/2014 | Miller-Moslin et al. |
| 8,865,901 B2 | 10/2014 | Hockenbery et al. |
| 8,937,193 B2 | 1/2015 | Pellecchia et al. |
| 10,195,213 B2 | 2/2019 | David |
| 2004/0242886 A1 | 12/2004 | Gupta et al. |
| 2004/0248877 A1 | 12/2004 | Gupta et al. |
| 2006/0252801 A1 | 11/2006 | Chen et al. |
| 2009/0105319 A1 | 4/2009 | Pellecchia et al. |
| 2009/0124675 A1 | 5/2009 | Pellecchia |
| 2010/0160322 A1 | 6/2010 | Bruncko et al. |
| 2010/0292200 A1 | 11/2010 | Kile et al. |
| 2011/0091552 A1 | 4/2011 | McCaffrey et al. |
| 2011/0218155 A1 | 9/2011 | Walensky et al. |
| 2011/0251188 A1 | 10/2011 | Zhang et al. |
| 2012/0028925 A1 | 2/2012 | Tao et al. |
| 2012/0108590 A1 | 5/2012 | Birtalan et al. |
| 2012/0129853 A1 | 5/2012 | Elmore et al. |
| 2012/0172285 A1 | 7/2012 | Walensky et al. |
| 2012/0190688 A1 | 7/2012 | Bruncko et al. |
| 2012/0269901 A1 | 10/2012 | Reed et al. |
| 2012/0277210 A1 | 11/2012 | Catron et al. |
| 2013/0035304 A1 | 2/2013 | Walensky et al. |
| 2013/0096120 A1 | 4/2013 | Wang et al. |
| 2013/0096121 A1 | 4/2013 | Wang et al. |
| 2013/0184278 A1 | 7/2013 | Kunzer et al. |
| 2013/0267514 A1 | 10/2013 | Bruncko et al. |
| 2013/0267534 A1 | 10/2013 | Bruncko et al. |
| 2013/0295185 A1 | 11/2013 | Sebti et al. |
| 2013/0296295 A1 | 11/2013 | Bruncko et al. |
| 2014/0005190 A1 | 1/2014 | Baell et al. |
| 2014/0057889 A1 | 2/2014 | Bruncko et al. |
| 2014/0057890 A1 | 2/2014 | Bruncko et al. |
| 2014/0066621 A1 | 3/2014 | Bruncko et al. |
| 2014/0073640 A1 | 3/2014 | Judd et al. |
| 2014/0088106 A1 | 3/2014 | Bruncko et al. |
| 2014/0094471 A1 | 4/2014 | Bruncko et al. |
| 2014/0107119 A1 | 4/2014 | Bruncko et al. |
| 2014/0113910 A1 | 4/2014 | Bruncko et al. |
| 2014/0135318 A1 | 5/2014 | Borzilleri et al. |
| 2014/0275082 A1 | 9/2014 | Tao et al. |
| 2014/0343093 A1 | 11/2014 | Ford et al. |
| 2014/0350014 A1 | 11/2014 | Ford et al. |
| 2014/0357633 A1 | 12/2014 | Ford et al. |
| 2014/0357666 A1 | 12/2014 | Visser et al. |
| 2017/0056421 A1 | 3/2017 | Zhou et al. |

FOREIGN PATENT DOCUMENTS

| | | |
|---|---|---|
| WO | WO-2008017121 A1 | 2/2008 |
| WO | WO-2008017123 A1 | 2/2008 |
| WO | WO-2008030836 A2 | 3/2008 |
| WO | WO-2008061208 A2 | 5/2008 |
| WO | WO-2008113131 A1 | 9/2008 |
| WO | WO-2009036035 A1 | 3/2009 |
| WO | WO-2009036051 A1 | 3/2009 |
| WO | WO-2009039553 A1 | 4/2009 |
| WO | WO-2010024783 A1 | 3/2010 |
| WO | WO-2010065824 A2 | 6/2010 |
| WO | WO-2010065865 A2 | 6/2010 |
| WO | WO-2010067067 A1 | 6/2010 |
| WO | WO-2010080478 A1 | 7/2010 |
| WO | WO-2010080503 A1 | 7/2010 |
| WO | WO-2010083441 A2 | 7/2010 |
| WO | WO-2010083442 A1 | 7/2010 |
| WO | WO-2010138588 A2 | 12/2010 |
| WO | WO-2011029842 A1 | 3/2011 |
| WO | WO-2011068560 A1 | 6/2011 |
| WO | WO-2011068561 A1 | 6/2011 |
| WO | WO-2011119345 A2 | 9/2011 |
| WO | WO-2011146674 A2 | 11/2011 |
| WO | WO-2011149492 A1 | 12/2011 |
| WO | WO-2011150016 A1 | 12/2011 |
| WO | WO-2012009347 A2 | 1/2012 |
| WO | WO-2012031103 A2 | 3/2012 |
| WO | WO-2012058392 A1 | 5/2012 |
| WO | WO-2012071374 A1 | 5/2012 |
| WO | WO-2012121758 A1 | 9/2012 |
| WO | WO-2013052608 A1 | 4/2013 |
| WO | WO-2013055895 A1 | 4/2013 |
| WO | WO-2013055897 A1 | 4/2013 |
| WO | WO-2013096049 A1 | 6/2013 |
| WO | WO-2014028381 A1 | 2/2014 |
| WO | WO-2014047427 A2 | 3/2014 |
| WO | WO-2014110476 A2 | 7/2014 |
| WO | WO-2014158528 A1 | 10/2014 |
| WO | WO-2015031608 A1 | 3/2015 |
| WO | WO-2015116740 A1 | 8/2015 |
| WO | WO-2015171591 A1 | 11/2015 |

OTHER PUBLICATIONS

Chang, et al. Clearance of senescent cells by ABT263 rejuvenates aged hematopoietic stem cells in mice. Nat Med. Dec. 14, 2015.

Ianitti, et al. Intra-articular injections for the treatment of osteoarthritis: focus on the clinical use of hyaluronic acid. Drugs R D. 2011;11(1):13-27.

Office Action dated May 17, 2017 for U.S. Appl. No. 15/069,769.

Siddiqui, et al. The mystery of BCL2 family: Bcl-2 proteins and apoptosis: an update. Arch Toxicol. Mar. 2015;89(3):289-317. Epub Jan. 25, 2015.

UAMS News Bureau. UAMS Research Findings Show Radiation, Aging Effects Can Be Cleared with Drug; Findings Published in Nature Medicine. www.uamshealth.com/news. Dec. 14, 2015. 2 pages.

Uraoka, et al. Loss of bcl-2 during the senescence exacerbates the impaired angiogenic functions in endothelial cells by deteriorating the mitochondrial redox state. Hypertension. Aug. 2011;58(2):254-63 Epub Jul. 5, 2011.

Wang. Senescent human fibroblasts resist programmed cell death, and failure to suppress bcl2 is involved. Cancer Res. Jun. 1, 1995;55(11):2284-92.

CHEMICAL ENTITIES THAT KILL SENESCENT CELLS FOR USE IN TREATING AGE-RELATED DISEASE

CROSS-REFERENCE

This application is a continuation of U.S. patent application Ser. No. 15/069,769, filed Mar. 14, 2016, which claims the benefit of U.S. Provisional Patent Application No. 62/177,434, filed on Mar. 13, 2015, which is incorporated by reference in its entirety.

BACKGROUND

Cellular senescence is the irreversible growth arrest of mitotic cells that can lead to altered phenotypes, and consequently impair tissue function and predispose tissues to disease development. Senescent cells accumulate in tissues and organs as an individual ages, and are implicated in a variety of diseases and disorders, including aging-related diseases. The elimination of senescent cells can be a viable treatment for aging-related diseases.

SUMMARY OF THE INVENTION

In some embodiments, the invention provides a method for treating a senescent cell-associated condition, the method comprising administering to a subject in need thereof a therapeutically-effective amount of a compound described herein, or a pharmaceutically-acceptable salt thereof.

DETAILED DESCRIPTION

Aging is a risk factor for most chronic diseases, disabilities, and declining health. Senescent cells, which are cells in replicative arrest, accumulate as an individual ages and can contribute partially or significantly to cell and tissue deterioration that underlies aging and age related diseases. Cells can also become senescent after exposure to an environmental, chemical, or biological insult or as a result of a disease. Provided herein are methods and agents for selective killing of senescent cells that are associated with numerous pathologies and diseases, including age-related pathologies and diseases. As disclosed herein, senescent cell-associated diseases and disorders can be treated by administering a compound described herein, or a pharmaceutically-acceptable salt thereof.

A compound described herein can selectively destroy, kill, remove, or facilitate destruction of senescent cells. A compound described herein can destroy or kill a senescent cell in a biologically, clinically, or statistically-significant manner in contrast to a non-senescent cell. A compound described herein can be used in an amount and for a time sufficient that selectively kills established senescent cells but is insufficient to kill a non-senescent cell in a clinically significant or biologically significant manner. In some embodiments, a compound described herein alters at least one signaling pathway in a manner that induces, initiates, stimulates, triggers, activates, or promotes and results in death of the senescent cell. Assessment of the effectiveness of a compound described herein can include comparing the symptoms of the subject receiving treatment with a compound described herein with those of a subject without such treatment or with placebo treatment.

Indications

The senescent cell associated disease or disorder treated by a compound described herein includes a cardiovascular disease or disorder, inflammatory disease or disorder, pulmonary disease or disorder, neurological disease or disorder, metabolic disease or disorder, dermatological disease or disorder, a metastasis, a chemotherapy or radiotherapy-induced side effect, age-related disease or disorder, a premature aging disease or disorder, and a sleep disorder.

Cardiovascular Conditions

In some embodiments, the disclosure provides methods for treating a senescent cell-associated condition, the method comprising administering a therapeutically-effective amount of a compound described herein to a subject in need thereof, wherein the senescent cell-associated condition is a cardiovascular condition. Non-limiting examples of cardiovascular conditions, include, but are not limited to angina, arrhythmia, atherosclerosis, cardiomyopathy, congestive heart failure, coronary artery disease (CAD), carotid artery disease, endocarditis, heart attack, coronary thrombosis, myocardial infarction (MI), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease, peripheral artery disease (PAD), cardiac stress resistance, and stroke.

A cardiovascular condition can be associated with or caused by arteriosclerosis. An atherosclerotic plaque can be stabilized by administering a compound described herein to a subject in need thereof. In some embodiments, the atherosclerotic plaque is stabilized in a blood vessel, for example, an artery, of a subject, thereby reducing the likelihood of occurrence or delaying the occurrence of a thrombotic event, such as a stroke or MI. A compound described herein can reduce the lipid content or fibrous cap thickness of an atherosclerotic plaque in a subject in need thereof. Fibrous cap formation can occur from the migration and proliferation of vascular smooth muscle cells and from matrix depositions. A thin fibrous cap can contribute to plaque instability and to increased risk of rupture. Such methods can reduce the likelihood of occurrence or delay the occurrence of a thrombotic event, such as a stroke or MI.

A compound described herein can inhibit, reduce, or cause a decrease in the formation of an atherosclerotic plaque in a subject in need thereof, or reduce, decrease, or diminish the amount, or level, of a plaque in a subject in need thereof. Reduction in the amount of a plaque in a blood vessel, for example, an artery, can be determined, for example, by a decrease in surface area of the plaque, or by a decrease in the extent, degree, or percent occlusion of a blood vessel, for example an artery, which can be determined by angiography or other visualizing methods.

A compound described herein can increase, improve, promote, or enhance stability of an atherosclerotic plaque in a subject in need thereof.

The effectiveness of a compound described herein in treating a cardiovascular disease or disorder can be assessed by one or any combination of diagnostic methods, including physical examination and assessment, monitoring of clinical symptoms, and performance of analytical tests and methods. Analytical tests and methods include, but are not limited to, angiography, electrocardiography, stress test, or non-stress test.

Inflammatory and Autoimmune Conditions

In some embodiments, the disclosure provides methods for treating a senescent cell-associated condition, the method comprising administering a therapeutically-effective amount of a compound described herein to a subject in need thereof, wherein the senescent cell-associated condition is an inflammatory condition. Inflammatory conditions include, but are not limited to, osteoarthritis, osteoporosis, oral mucositis, rheumatoid arthritis, inflammatory bowel disease, kyphosis, herniated intervertebral disc, ulcerative colitis, Crohn's disease, ulcerative asthma, renal fibrosis, liver fibrosis, pancreatic fibrosis, cardiac fibrosis, skin wound healing, and oral submucous fibrosis.

In some embodiments, the disclosure provides methods for treating or reducing the likelihood of conditions resulting from a host immune response to an organ transplant in a subject in need thereof. Non-limiting examples of an organ transplant include a kidney organ transplant, a bone marrow transplant, a liver transplant, a lung transplant, and a heart transplant. In some embodiments, the disclosure provides methods for treating graft-vs-host disease in a subject in need thereof.

In some embodiments, the disclosure provides methods for reducing or inhibiting loss or erosion of proteoglycan layers in a joint in a subject in need thereof. The disclosure provides methods for reducing inflammation in an inflamed joint in a subject in need thereof. A compound described herein can stimulate, enhance, or induce production of collagen in a subject in need thereof, for example, type 2 collagen. A compound described herein can reduce an amount, or level, of an inflammatory cytokine in a subject in need thereof, for example, IL-6. A compound described herein can decrease, inhibit, or reduce the production of metalloproteinase 13 (MMP-13) in a subject in need thereof. A compound described herein can reduce the likelihood of, inhibit, or decrease the erosion of bone in a subject in need thereof. A compound described herein can be administered directly to an osteoarthritic joint, for example, intraarticularly, topically, transdermally, intradermally, or subcutaneously. A compound described herein can restore, improve, or inhibit deterioration of strength of a joint in a subject in need thereof. A compound described herein can reduce joint pain in a subject in need thereof. In some embodiments, the joint is an osteoarthritic joint.

The effectiveness of a compound described herein in treating an inflammatory condition can be assessed by one or any combination of diagnostic methods, including physical examination, assessment and monitoring of clinical symptoms, and performance of analytical tests to monitor the health status of a subject. Physical examination can include, for example, determining tenderness, swelling or redness of the affected joint, and assessment and monitoring of clinical symptoms. Performance of analytical tests and methods can include, for example, determining the level of inflammatory cytokines or chemokines, X-ray images to determine loss of cartilage as shown by a narrowing of space between the bones in a joint, magnetic resonance imaging (MRI), and providing detailed images of bone and soft tissues.

Pulmonary Conditions

In some embodiments, the disclosure provides methods for treating a senescent cell-associated condition, the method comprising administering a therapeutically-effective amount of a compound described herein to a subject in need thereof, wherein the senescent cell-associated condition is a pulmonary condition. Pulmonary conditions include, but are not limited to, idiopathic pulmonary fibrosis (IPF), chronic obstructive pulmonary disease (COPD), asthma, cystic fibrosis, bronchiectasis, and emphysema.

In some embodiments, the subject has been exposed to environmental pollutants, for example, silica. A subject can be exposed to an occupational pollutant, for example, dust, smoke, asbestos, or fumes. In some embodiments, the subject has smoked cigarettes.

In some embodiments, the subject has a connective tissue disease. The connective tissue disease can be, for example, rheumatoid arthritis, systemic lupus erythematosus, scleroderma, sarcoidosis, or Wegener's granulomatosis. In some embodiments, the subject has an infection. In some embodiments, the subject has taken or is taking medication or has received radiation therapy to the chest. The medication can be, for example, amiodarone, bleomycin, busufan, methotrexate, or nitrofurantoin.

The effectiveness of a compound described herein in treating a pulmonary condition can be assessed by one or any combination of diagnostic methods including physical examination, determination of patient's medical history, determination of patient's family's medical history, chest X-ray, lung function test, spirometry test, blood test, arterial blood gas analysis, bronchoalveolar lavage, lung biopsy, CT scan, and exercise testing. Methods and techniques that evaluate mechanical functioning of the lung, for example, techniques that measure lung capacitance, elastance, and airway hypersensitivity can be performed. To determine lung function and to monitor lung function throughout treatment, any one of numerous measurements can be obtained, for example, expiratory reserve volume (ERV), forced vital capacity (FVC), forced expiratory volume (FEV) (e.g., FEV in one second, FEV1), FEV1/FEV ratio, forced expiratory flow 25% to 75%, maximum voluntary ventilation (MVV), peak expiratory flow (PEF), and slow vital capacity (SVC). Total lung volumes include total lung capacity (TLC), vital capacity (VC), residual volume (RV), and functional residual capacity (FRC). Gas exchange across alveolar capillary membrane can be measured using diffusion capacity for carbon monoxide (DLCO). Peripheral capillary oxygen saturation ($SpO_2$) can also be measured. Normal oxygen levels can be between 95% and 100%. An $SpO_2$ level below 90% can suggest that the subject has hypoxemia. Values below 80% can be critical and require intervention to maintain brain and cardiac function and avoid cardiac or respiratory arrest.

Neurological Conditions

In some embodiments, the disclosure provides methods for treating a senescent cell-associated condition, the method comprising administering a therapeutically-effective amount of a compound described herein to a subject in need thereof wherein the senescent cell-associated condition is a neurological condition. Neurological conditions include, but are not limited to, Parkinson's disease, Alzheimer's disease, dementia, amyotrophic lateral sclerosis (ALS), bulbar palsy, pseudobulbar palsy, primary lateral sclerosis, motor neuron dysfunction (MND), mild cognitive impairment (MCI), Huntington's disease, ocular diseases, age-related macular degeneration, glaucoma, vision loss, presbyopia, cataracts, progressive muscular atrophy, lower motor neuron disease, spinal muscular atrophy (SMA), Werdnig-Hoffman Disease (SMA1), SMA2, Kugelberg-Welander Disease (SM3), Kennedy's disease, post-polio syndrome, and hereditary spastic paraplegia.

Non-limiting examples for monitoring the effect of a therapy on inhibiting progression of glaucoma include automated perimetry, gonioscopy, imaging technology, scanning laser tomography, HRT3, laser polarimetry, GDX, ocular coherence tomography, ophthalmoscopy, and pachymeter measurements that determine central corneal thickness.

A compound described herein can delay or inhibit the onset of cataracts, presbyopia, and macular degeneration in a subject in need thereof who is at risk for developing cataracts, presybopia, and macular degeneration. In some embodiments, the subject is a human subject who is at least 40 years of age.

The effectiveness of a compound described herein in treating a neurological condition can be assessed by one or any combination of diagnostic methods including physical examination, assessment and monitoring of clinical symptoms, and performance of analytical tests and methods described herein Metabolic Conditions In some embodiments, the disclosure provides methods for treating a senescent cell-associated conditions, the method comprising administering a therapeutically-effective amount of a compound described herein to a subject in need thereof wherein the senescent cell-associated condition is a metabolic condition. Metabolic conditions include, but are not limited to, diabetes (Type 1 or Type 2), metabolic syndrome, diabetic ulcers, obesity, renal dysfunction, nephrological pathology, and glomerular disease.

The effectiveness of a compound described herein in treating a metabolic condition can be assessed by one or any combination of diagnostic methods including physical examination assessment and monitoring of clinical symptoms, and performance of analytical tests and methods, such as those described herein. A subject who is receiving a compound described herein for treatment or reduction in the likelihood of developing diabetes can be monitored, for example, by assaying glucose and insulin tolerance, energy expenditure, body composition, fat tissue, skeletal muscle, and liver inflammation, or lipotoxicity.

Dermatological Conditions

In some embodiments, the disclosure provides methods for treating a senescent cell-associated condition, the method comprising administering a therapeutically-effective amount of a compound described herein to a subject in need thereof wherein the senescent cell-associated condition is a dermatological condition. Dermatological conditions include, but are not limited to, psoriasis, eczema, rhytides, pruritis, dysesthesia, papulosquamous disorders, erythroderma, lichen planus, lichenoid dermatosis, atopic dermatitis, eczematous eruptions, eosinophilic dermatosis, reactive neutrophilic dermatosis, pemphigus, pemphigoid, immunobullous dermatosis, fibrohistocytic proliferations of skin, cutaneous lymphomas, and cutaneous lupus.

The effectiveness of a compound described herein in treating a dermatological condition can be assessed by one or any combination of diagnostic methods including physical examination assessment and monitoring of clinical symptoms, and performance of analytical tests and methods, such as those described herein.

Metastasis

In some embodiments, the disclosure provides methods for treating a senescent cell-associated condition, the method comprising administering a therapeutically-effective amount of a compound described herein to a subject in need thereof wherein the senescent cell-associated condition comprises metastasis, such as metastasis of a cancer.

A compound described herein can reduce the likelihood of metastasis in a subject in need thereof. The compound described herein can be administered one or more days within a window of treatment. In some embodiments, the treatment window is 1, 2, 3, 4, 5, 6, 7, 8, 9, 10, 11, 12, 13, 14, 15, 16, 17, 18, 19, 20, or 21 days. In some embodiments, a compound described herein is administered on two or more days within a treatment window of no longer than 7 days or 14 days; on 3 or more days within a treatment window of no longer than 7 days or 14 days; on 4 or more days within a treatment window of no longer than 7 days or 14 days; on 5 or more days within a treatment window of no longer than 7 days or 14 days; or on 6, 7, 8, 9, 10, 11, 12, 13, or 14 days within treatment window of no longer than 7 days or 14 days.

Chemotherapy and radiotherapy treatment regimens can comprise a finite number of cycles of on-drug therapy followed by off-drug therapy, or comprise a finite timeframe in which the chemotherapy or radiotherapy is administered. The protocols can be determined by clinical trials, drug labels, and clinical staff in conjunction with the subject to be treated. The number of cycles of a chemotherapy or radiotherapy or the total length of time of a chemotherapy or radiotherapy regimen can vary depending on the subject's response to the cancer therapy. A compound described herein can be administered after the treatment regimen of chemotherapy or radiotherapy has been completed.

In some embodiments, the metastasis is a solid tumor. In some embodiments, the metastasis is a liquid tumor. Cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein can also be used for inhibiting progression of metastatic cancer tumors. Non-limiting examples of cancers include adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (cml), hairy cell leukemia, lip cancer, liver cancer (primary), childhood liver cancer (primary), lobular carcinoma in situ (LCIS), lung cancer, non-small cell lung cancer, small cell lung cancer, lymphoma, aids-related lymphoma, burkitt lymphoma, cutaneous t-cell lymphoma, Hodgkin lymphoma, non-Hodgkin lymphoma, primary central nervous system lymphoma (CNS), melanoma, childhood melanoma, intraocular melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sézary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, and Waldenström macroglobulinemia.

Chemotherapy and Radiotherapy Side Effects

In some embodiments, the disclosure provides methods for treating a senescent cell-associated condition, the method comprising administering a therapeutically-effective amount of a compound described herein to a subject in need thereof wherein the senescent cell-associated condition is a chemotherapy-induced or radiotherapy-induced side effect. Non-limiting examples of chemotherapeutic agents include anthracyclines, doxorubicin, daunorubicin, taxols, paclitaxel, gemcitabine, pomalidomide, and lenalidomide. Chemotherapy-induced side effects or radiotherapy-induced side effects include, but art not limited to, weight loss, endocrine changes, hormone imbalance, changes in hormone signaling, changes is cardiotoxicity, body composition, reduced ability to be physically active, gastrointestinal toxicity, nausea, vomiting, constipation, anorexia, diarrhea, peripheral neuropathy, fatigue, malaise, low physical activity, hematological toxicity, anemia, hepatotoxicity, alopecia, pain, infection, mucositis, fluid retention, dermatological toxicity, rashes, dermatitis, hyperpigmentation, urticaria, photosensitivity, nail changes, mouth, gum or throat problems, and any toxic side effect caused by a chemotherapy or radiotherapy. In some embodiments, the disclosure provides methods for treating or reducing the likelihood of metastasis comprising administering a compound described herein during an off-chemotherapy or off-radiotherapy time interval or after the chemotherapy or radiotherapy treatment regimen has been completed.

In some embodiments, the chemotherapy-induced side effect is cardiotoxicity and is caused by anthracycline.

In some embodiments, the disclosure provides methods for treating chronic or long term chemotherapy-induced or radiotherapy-induced side effects. Certain toxic effects can appear long after treatment and can result from damage to an organ or system by the therapy. Organ dysfunction, for example, neurological, pulmonary, cardiovascular, and endocrine dysfunction, can be observed in subjects who were treated for cancers during childhood. Chronic or late toxic side effects that occur in subjects who received chemotherapy or radiation therapy include, for example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

Age-Related Conditions

In some embodiments, the disclosure provides methods for treating a senescent cell-associated condition, the method comprising administering a therapeutically-effective amount of a compound described herein to a subject in need thereof wherein the senescent cell-associated condition is an age-related condition. In some embodiments, the age-related condition is caused by exposure to an agent or factor such as irradiation, chemotherapy, smoking tobacco, high-fat/high sugar diet, or other environmental factor. Age-related diseases and disorders include, but are not limited to, herniated intervertebral disc, frailty, hair loss, hearing loss, vision loss, muscle fatigue, skin conditions, skin nevi, wrinkly skin, hyperpigmentation, scarring, keloid, rosacea, vitiligo, ichthyosis vulgaris, dermatomyositis, actinic keratosis, and sarcopenia.

In some embodiments, the disclosure provides methods for extending the lifespan of a mammal comprising administering to a subject a compound described herein.

The effectiveness of a compound described herein in treating an age-related condition can be assessed by one or any combination of diagnostic methods including physical examination, patient self-assessment, assessment and monitoring of clinical symptoms, performance of analytical tests and methods, including clinical laboratory tests, physical tests, and exploratory surgery.

Erdheim-Chester Disease

In some embodiments, the disclosure provides methods for treating a senescent cell-associated condition, the method comprising administering a compound described herein to a subject in need thereof wherein the senescent cell-associated condition is Erdheim-Chester Disease. Erdheim-Chester disease (ECD) (also known as Erdheim-Chester syndrome or polyostotic sclerosing histiocytosis) is a rare disease characterized by the abnormal multiplication of a specific type of white blood cells called histiocytes, or tissue macrophages. Usually, the onset of ECD is in middle age. ECD involves an infiltration of lipid-laden macrophages, multinucleated giant cells, an inflammatory infiltrate of lymphocytes and histiocytes in the bone marrow, and a generalized sclerosis of the long bones. Radiologic osteosclerosis and histology can be diagnostic features for ECD. Video-assisted thoracoscopic surgery can be used for diagnostic confirmation and also for therapeutic relief of recurrent pericardial fluid drainage.

Premature Aging Conditions

In some embodiments, the disclosure provides methods for treating a senescent cell-associated condition, the method comprising administering a therapeutically-effective amount of a compound described herein to a subject in need thereof wherein the senescent cell-associated condition is a premature aging disease or disorder. Premature aging diseases and disorders include, but are not limited to Hutchinson-Gilford progeria or Werner's Syndrome.

Sleep Conditions

In some embodiments, the disclosure provides methods for treating a senescent cell-associated condition, the method comprising administering a therapeutically-effective amount of a compound described herein to a subject in need thereof wherein the senescent cell-associated condition is a sleep condition. Sleep conditions include, but are not limited to, sleep apnea, hypersomnia, cataplexy, sleep fragmentation, sleeping sickness, sleepwalking, night terrors, bed wetting, bruxism, delayed sleep phase disorder (DSPD), hypopnea syndrome, idiopathic hypersomnia, insomnia, Kleine-Levin syndrome, narcolepsy, excessive daytime sleepiness, nocturia, parasomnias, periodic limb movement disorder, nocturnal myoclonus, hypnic jerk, rapid eye movement sleep behavior disorder, restless leg syndrome, obstructive sleep apnea, sleep paralysis, sleepwalking, somniphobia, situational circadian rhythm sleep disorder, shift worker sleep disorder, and jet lag.

Compounds

In some embodiments, the compound is selected from any of the compounds listed in related application U.S. patent application Ser. No. 15/069,769, published as US 2017/0281649 A1, to which this disclosure claims priority. The entire contents of U.S. patent application Ser. No. 15/069,769 are hereby incorporated herein in its entirety for all purposes, including but not limited to the structure of all the compounds listed therein and their preparation and use for killing senescent cells and treating age-related diseases.

The composition can be formulated with one or more pharmaceutically-acceptable excipients in the form of a pharmaceutical formulation.

A compound described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis.

The invention provides the use of pharmaceutically-acceptable salts of any therapeutic compound described herein. Pharmaceutically-acceptable salts include, for example, acid-addition salts and base-addition salts. The acid that is added to a compound described herein to form an acid-addition salt can be an organic acid or an inorganic acid. A base that is added to a compound described herein to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound described herein of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound described herein of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Formulations

A pharmaceutical composition of the disclosure can be a combination of any pharmaceutical formulation of a compound described herein with other chemical components, such as carriers, stabilizers, diluents, dispersing agents, suspending agents, thickening agents, and/or excipients. The pharmaceutical composition facilitates administration of a compound described herein to an organism. Pharmaceutical compositions can be administered in therapeutically-effective amounts as pharmaceutical compositions by any form and route known in the art including, for example, intravenous, subcutaneous, intramuscular, oral, rectal, parenteral, ophthalmic, pulmonary, transdermal, vaginal, otic, nasal, and topical administration.

A pharmaceutical composition can be administered in a local or systemic manner, for example, via injection of a compound described herein directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining a compound described herein with pharmaceutically acceptable carriers or excipients. Such carriers can be used to formulate liquids, gels, syrups, elixirs, slurries, or suspensions for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a compound described herein in water-soluble form. Suspensions of a compound described herein can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of a compound described herein to allow for the preparation of highly concentrated solutions. Alternatively, the active ingredient can be in powder form for constitution with a suitable vehicle, e.g., sterile pyrogen-free water, before use.

A compound described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

A compound described herein can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, is first melted.

In practicing the methods of treatment or use provided herein, therapeutically-effective amounts of a compound described herein is administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of a compound described herein used, and other factors.

Pharmaceutical compositions can be formulated using one or more physiologically-acceptable carriers comprising excipients and auxiliaries, which facilitate processing of a compound described herein into preparations that can be used pharmaceutically. Formulation can be modified depending upon the route of administration chosen. Pharmaceutical compositions comprising a compound described herein can be manufactured in a conventional manner, for example, by means of conventional mixing, dissolving, granulating, or emulsifying.

The pharmaceutical compositions can include at least one pharmaceutically acceptable carrier, diluent, or excipient and a compound described herein or pharmaceutically-acceptable salt form.

Methods for the preparation of compositions comprising a compound described herein can include formulating a compound described herein with one or more inert, pharmaceutically-acceptable excipients. Liquid compositions include, for example, solutions in which a compound described herein is dissolved, emulsions comprising a compound described herein, or a solution containing liposomes, micelles, or nanoparticles comprising a compound described herein as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

A compound described herein can be delivered via liposomal technology. The use of liposomes as drug carriers can increase the therapeutic index of a compound described hereins. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing

Pharmaceutical compositions described herein can be in unit dosage forms suitable for single administration of precise dosages. In unit dosage form, the formulation is divided into unit doses containing appropriate quantities of one or more compounds described herein. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound described herein is present in a composition in an amount ranging from about 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

The foregoing ranges are merely suggestive. Dosages can be altered depending on a number of variables, including, for example, the activity of a compound used, the disease or condition to be treated, the mode of administration, the requirements of the individual subject, the severity of the disease or condition being treated, and the judgment of the practitioner.

In some embodiments, are methods for treating diseases or disorders comprising administering a compound described herein to a subject in need thereof. In some embodiments, a compound described herein is administered in a manner that would be considered ineffective for treating any condition herein. In some embodiments, a compound described herein is administered in a decreased cumulative dose, over multiple therapeutic cycles compared with the amount required for cancer therapy.

In some embodiments, a compound described herein is administered within a treatment cycle, which treatment cycle comprises a treatment course followed by a non-treatment interval. One or more doses of a compound described herein can be administered on one or more days.

In some embodiments, the methods comprise administering a compound described herein in at least two treatment cycles. A non-treatment interval can be at least about 2 weeks or about 0.5 to about 12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. The non-treatment interval can be about 1 to about 2 years or about 1 to about 3 years, or longer. Each treatment course can be, for example, no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

In some embodiments, the treatment window is about one day. In some embodiments, a single treatment course occurs over no longer than 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days. During such treatment windows, a compound described herein can be administered at least on 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days with a variable number of days on which a compound described herein is not administered. For example, administration can be discontinued for 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days, and a discontinuation can occur at any time during the protocol. Intervals can be chosen as appropriate for the disease being treated, a compound described herein being administered, the health status of the subject, and other relevant factors.

A daily dose of a compound described herein can be a single administration or the dose can be divided into 2, 3, 4, or 5 separate administrations to provide the total daily dose of a compound described herein.

A treatment cycle can be repeated as often as needed. For example, a treatment cycle can be repeated at least once, at least twice, at least three times, at least four times, at least five times, at least six times, at least seven times, at least eight times, at least nine times, at least ten times, or more often as needed. Consecutive cycles can have the same, similar, or different durations, dosages, or protocols. Treatment course or a treatment cycle can be repeated, such as when the disease or disorder recurs, or when symptoms or sequelae of the disease or disorder that were significantly diminished by one treatment course as described above have increased or are detectable, or when the symptoms or sequelae of the disease or disorder are exacerbated, a treatment course can be repeated.

A compound described herein can be administered to a subject to reduce likelihood of occurrence or development, or to delay onset, progression, or severity of the disease, and a cycle useful for that purpose can be administered.

In some embodiments, a compound described herein is administered in a treatment window comprising 21 days. In some embodiments, a compound described herein is administered daily for 14 days followed by 7 days off. In some embodiments, a compound described herein is administered daily for 13 days followed by 8 days off In some embodiments, a compound described herein is administered daily for 12 days followed by 9 days off. In some embodiments, a compound described herein is administered daily for 11 days followed by 10 days off. In some embodiments, a compound described herein is administered daily for 10 days followed by 11 days off. In some embodiments, a compound described herein is administered daily for 9 days followed by 12 days off. In some embodiments, a compound described herein is administered daily for 8 days followed by 13 days off In some embodiments, a compound described herein is administered daily for 7 days followed by 14 days off. In some embodiments, a compound described herein is administered daily for 6 days followed by 15 days off. In some embodiments, a compound described herein is administered daily for 5 days followed by 16 days off In some embodiments, a compound described herein is administered daily for 4 days followed by 17 days off. In some embodiments, a compound described herein is administered daily for 3 days followed by 18 days off. In some embodiments, a compound described herein is administered daily for 2 days followed by 19 days off. In some embodiments, a compound described herein is administered for 1 day followed by 20 days off In some embodiments, a compound described herein is administered daily for about 21, about 14, or about 7 days in a dose of about 150 mg to about 325 mg. In some embodiments, a compound described herein is administered daily for about 21, about 14, or about 7 days in a dose of about 150 mg to about 300 mg. In some embodiments, a compound described herein is administered daily for about 21, about 14, or about 7 days in a dose of about 150 mg to about 275 mg. In some embodiments, a compound described herein is administered daily for about 21, about 14, or about 7 days in a dose of about 150 mg to about 250 mg. In some embodiments, a compound described herein is administered daily for about 21, about 14, or about 7 days in a dose of about 150 mg to about 225 mg. In some embodiments, a compound described herein is administered daily for about 21, about 14, or about 7 days in a dose of about 150 mg to about 200 mg. In some embodiments, a compound described herein is administered daily for about 21, about 14, or about 7 days in a dose of about 150 mg to about 175 mg. In some embodiments, a compound described herein is administered daily for about 21, about 14, or about 7 days in a dose of about 150 mg. In some embodiments, a compound described herein is administered daily for about 21, about 14, or about 7 days in a dose of about 125 mg. In some embodiments, a compound described herein is administered daily for about 21, about 14, or about 7 days in a dose of about 100 mg. In some embodiments, a compound described herein is administered daily for about 21, about 14, or about 7 days in a dose of about 75 mg. In some embodiments, a compound described herein is administered daily for about 21, about 14, or about 7 days in a dose of about 50 mg. In some embodiments, a compound described herein is administered daily for about 21, about 14, or about 7 days in a dose of about 25 mg.

In some embodiments, a compound described herein is administered in a treatment window of 28 days. In some embodiments, a compound described herein is administered daily for 10 days, followed by 18 days off, daily for 9 days, followed by 19 days off, daily for 8 days, followed by 20 days off daily for 7 days, followed by 21 days off, daily for 6 days, followed by 22 days off, daily for 5 days, followed by 23 days off, daily for 4 days, followed by 24 days off, daily for 3 days, followed by 25 days off daily for 2 days, followed by 26 days off, or for 1 day, followed by 27 days off.

In some specific embodiments, a compound described herein is administered daily for about 10 days in a dose of about 20 mg/m$^2$, about 19 mg/m$^2$, about 18 mg/m$^2$, about 17 mg/m$^2$, about 16 mg/m$^2$, about 15 mg/m$^2$, about 14 mg/m$^2$, about 13 mg/m$^2$, about 12 mg/m$^2$, about 11 mg/m$^2$, about 10 mg/m$^2$, about 9 mg/m$^2$, about 8 mg/m$^2$, about 7 mg/m$^2$, about 6 mg/m$^2$, about 5 mg/m$^2$, about 4 mg/m$^2$, about 3 mg/m$^2$, about 2 mg/m$^2$, about 1 mg/m$^2$, about 0.75 mg/m$^2$, about 0.5 mg/m$^2$, about 0.25 mg/m$^2$, about 0.1 mg/m$^2$, or about 0.01 mg/m$^2$. A compound described herein can be administered for 5, 6, 7, 8, 9, 10, 11, 12, 13, or 14 days at the doses described above.

EXAMPLES

Example 1

Efficacy of a Test Compound in an Animal Model of Osteoarthritis

C57BL/6J mice undergo surgery to cut the anterior cruciate ligament of one rear limb to induce osteoarthritis in the joint of that limb. At week 2 post-surgery, mice receive 2.5 μg of test compound to the operated knee by intra-articular injection, qd for 5 days, with a second treatment (2.5 μg test compound-qd for 5 days) during week 4 post-surgery. At the end of 4 weeks post-surgery, operated joints of the mice are assessed for function, monitored for markers of inflammation, and undergo histological assessment.

Two control groups of mice are included: one group comprising C57BL/6J mice that undergo a sham surgery, for example, surgical procedures are followed except for cutting the ACL, and receive intra-articular injections of vehicle parallel to the treated group; and one group comprising C57BL/6J that undergo an ACL surgery and receive intra-articular injections of vehicle.

Function of the limbs are assessed at 4 weeks post-surgery by a weight bearing test to determine which leg the mice favor. The mice are allowed to acclimate to the chamber on at least 3 occasions prior to taking measurements. Mice are maneuvered inside the chamber to stand with 1 hind paw on each scale. The weight that is placed on each hind limb is measured over a 3-second period. At least 3 separate measurements are made for each animal at each time point. The results are expressed as the percentage of the weight placed on the operated limb versus the contralateral unoperated limb.

The function of the limbs are also assessed at 4 weeks post-surgery by hotplate analysis to show sensitivity and reaction to pain stimulus. In brief, a mouse is placed on a hotplate at 55° C. When placed on the hot surface of the plate, mice will lift their paws and lick them (paw-lick response) due to attainment of pain threshold. The latency period for the hind limb response (paw-lick response) is recorded as response time.

Histopathology of the proteoglycan layer is also analyzed.

Example 2

Efficacy of a Test Compound in an Animal Model of Cardiac Stress Resistance

At 12 months of age, mice are injected three times per week with a test compound, while a control group receives vehicle. At 18 months, subsets of male and female mice are subjected to a cardiac stress test, in which mice are injected with a lethal dose of isoproterenol (680 mg/kg) and the time to cardiac arrest is recorded. The time to cardiac arrest is compared between treated and untreated animals.

Example 3

Efficacy of a Test Compound in an Animal Model of Atherosclerosis

LDL$^{-/-}$ mice from 10 weeks of age are fed a high fat diet having 42% calories from fat beginning at Week 0 until Week 12.5. The mice are then switched to a normal chow diet. Mice are treated with a test compound or a vehicle from week 12.5 over the next 100 days, with each treatment cycle comprising 5 days of test compound described herein (25 mg/kg intraperitoneally daily) and 14 days off. At the end of the 100 day treatment period, mice are sacrificed, plasma and tissues are collected, and atherosclerosis is quantitated. Descending aortas are dissected and stained with Sudan IV to visualize the plaque lipids. The percentage of the aorta covered in plaques is measured by area, and is compared between the treated and untreated animals.

Example 4

Efficacy of a Test Compound in Animal Models of Pulmonary Disease

To assess the efficacy of a test compound in treating pulmonary diseases, a model of bleomycin-induced injury is used. In this model, mice develop lung fibrosis within 7-14 days after bleomycin treatment.

Bleomycin is administered to anesthetized 6-8 week-old mice by intratracheal aspiration (2.5 U/kg of bleomycin in 50 μl PBS) using a microsprayer syringe. Control mice are administered saline. The day following bleomycin treatment, a test compound (25 mg/kg in PBS) or vehicle is administered. Mice are treated via intraperitoneal injection for 5 consecutive days, followed by 5 days of rest, followed by a second treatment cycle of 5 consecutive days. Untreated mice receive an equal volume of vehicle. At 7, 14, and 21 days post-bleomycin treatment, lung function is assessed by monitoring oxygen saturation using the MouseSTAT PhysioSuite pulse oximeter. Animals are anesthetized with isoflurane (1.5%) and a toe clip is applied. Mice are monitored for 30 seconds and the average peripheral capillary oxygen saturation (SpO$_2$) measurement over this duration is calculated.

At 21 days post-bleomycin treatment, airway hyper-reactivity (AHR) of mice is examined. AHR of mice is measured by methacholine challenge while other parameters of lung function (airway mechanics, lung volume and lung compliance) are determined using a ventilator. While under ketamine/xylazine anesthesia and subjected to cannulation of the trachea via a tracheostomy (19 Fr blunt Luer cannula), airway resistance (elastance) and compliance of mice are assessed at baseline and in response to increasing concentrations of methacholine (0 to 50 mg/mL in PBS) delivered via nebulization. Animals are maintained at 37° C., and while under muscle paralysis (pancuronium); airway function is measured by using a ventilator and lung mechanics system.

Mice are euthanized by i.p injection of pentobarbital. Bronchoalveolar lavage (BAL) fluids and lungs are obtained and analyzed. Hydroxyproline content of lungs is measured and quantitative histopathology is performed.

In a second animal model for pulmonary diseases (e.g., COPD), mice are exposed to cigarette smoke. The effect of a test compound on the mice exposed to smoke is assessed by lung function and histopathology.

Six week-old mice are chronically exposed to cigarette smoke from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. Mice receive a total of 6 hours of cigarette smoke exposure per day, 5 days a week for 6 months. Each lighted cigarette is puffed for 2 seconds and once every minute for a total of 8 puffs, with the flow rate of 1.05 L/min, to provide a standard puff of 35 $cm^3$. The smoke machine is adjusted to produce a mixture of side stream smoke (89%) and mainstream smoke (11%) by smoldering 2 cigarettes at one time. The smoke chamber atmosphere is monitored for total suspended particulates (80-120 $mg/m^3$) and carbon monoxide (350 ppm). Beginning at day 7, mice are treated with a test compound or vehicle (3× per week) (5 consecutive days of treatment followed by 16 days off drug, repeated until the end of the experiment), respectively. An equal number of mice received the corresponding vehicle.

After two months of cigarette smoke exposure, lung function is assessed by monitoring oxygen saturation using the MouseSTAT PhysioSuite pulse oximeter. Animals are anesthetized with isoflurane (1.5%) and the toe clip is applied. Mice are monitored for 30 seconds and the average peripheral capillary oxygen saturation ($SpO_2$) measurement over this duration is calculated.

At the end of the experimental period, airway hyperreactivity (AHR) of mice to methacholine challenge using a ventilator and lung mechanics system is examined as described above. After AHR measurement, mice are killed by i.p. injection of pentobarbital for in-depth analysis of lung histopathology. Briefly, lungs are inflated with 0.5% low-melting agarose at a constant pressure of 25 cm. Lungs are fixed in 10% buffered formalin and embedded in paraffin. Sections (5 μm) are stained with hematoxylin and eosin. Mean alveolar diameter, alveolar length, and mean linear intercepts are determined by computer-assisted morphometry with Image Pro Plus software.

Example 5

Efficacy of a Test Compound in Treating Chemotherapy-Induced Side Effects

Paclitaxel is administered to mice. Groups of mice (n=4) are treated three times every two days with 20 mg/kg paclitaxel or vehicle. Two days after the third dose of paclitaxel, a test compound is administered daily for three days (days 1, 2, and 3) intraperitoneally at 25 mg/kg. Two days after the last dose of a test compound, all groups of animals are housed in metabolic cages to monitor voluntary exercise as determined by wheel counts. Data are collected and analyzed two days later. Wheel count reduction as caused by chemotherapy is observed for restoration by the test compound.

Example 6

Efficacy of a Test Compound in Improving Glucose Tolerance and Insulin Sensitivity Groups of mice (n=9) are fed a high fat diet for four months mice or a regular chow diet. Animals are then treated with a test compound (3 rounds of 25 mg/kg test compound administered daily for five consecutive days) or vehicle. A glucose bolus is given at time zero, and blood glucose is monitored at 20, 30, 60, and 120 minutes after delivering glucose to determine glucose disposal. AUC is quantitated, with a higher AUC value indicating glucose intolerance. Hemoglobin A1c level is also measured for assessing glucose tolerance. Insulin sensitivity is also determined (Insulin Tolerance Testing (ITT)). Changes in weight, body composition, and food intake are also monitored.

What is claimed is:

1. A method of killing a senescent cell, the senescent cell being characterized as a non-cancerous cell in replicative arrest, the method comprising contacting the senescent cell with an effective amount of a senolytic compound that is lethal to the senescent cell, wherein the senolytic compound is gambogic acid or a pharmaceutical salt thereof.

2. The method of claim 1, wherein the senescent cell is a fibroblast.

3. The method of claim 1, wherein the senescent cell is a preadipocyte.

4. The method of claim 1, wherein the senescent cell is a chondrocyte.

5. A method of killing senescent cells in a mixed cell population, the senescent cells being characterized as non-cancerous cells in replicative arrest, the method comprising administering to the mixed cell population an effective amount of a senolytic compound, wherein the senolytic compound is gambogic acid or a a pharmaceutical salt thereof.

6. The method of claim 5, wherein the mixed cell population is present in an organ or tissue.

7. The method of claim 5, wherein the compound kills at least 25% of the senescent cells in the mixed cell population.

8. The method of claim 5, wherein the compound is administered to the mixed cell population in a timed-release formulation.

* * * * *